US010175241B2

(12) United States Patent
Andres et al.

(10) Patent No.: US 10,175,241 B2
(45) Date of Patent: Jan. 8, 2019

(54) ASC AS A MARKER FOR LUNG CANCER (75) Inventors: Herbert Andres, Penzberg (DE); Marie-Luise Hagmann, Penzberg (DE); Johann Karl, Peissenberg (DE); Markus Roessler, Germering (DE); Michael Tacke, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 613 days.

(21) Appl. No.: 12/968,784

(22) Filed: Dec. 15, 2010

(65) Prior Publication Data
US 2011/0171676 A1 Jul. 14, 2011

Related U.S. Application Data (63) Continuation of application No. PCT/EP2009/004765, filed on Jul. 1, 2009.

(30) Foreign Application Priority Data

Jul. 3, 2008 (EP) .................................... 08012070

(51) Int. Cl.
*G01N 33/574* (2006.01)
(52) U.S. Cl.
CPC .............. *G01N 33/57423* (2013.01); *G01N 2333/4742* (2013.01)
(58) Field of Classification Search
CPC ................ G01N 33/57423; G01N 2333/4742
See application file for complete search history.

(56) References Cited

U.S. PATENT DOCUMENTS

2006/0257952 A1* 11/2006 Pestlin et al. ................ 435/7.23

FOREIGN PATENT DOCUMENTS

| CN | 1977052 A | 6/2007 |
|---|---|---|
| JP | 2006-61002 A | 3/2006 |
| WO | 2001/029235 A3 | 4/2001 |
| WO | 2005040806 A2 | 5/2005 |
| WO | 2006066915 A1 | 6/2006 |
| WO | 2006066917 A1 | 6/2006 |
| WO | 2008014951 A1 | 2/2008 |
| WO | 2008/063655 A3 | 5/2008 |

OTHER PUBLICATIONS

Greenberg et al, Biomarkers for lung cancer: clinical uses, Current Opinion in Pulmonary Medicine, 2007, vol. 13, pp. 249-255.*
Masumoto et al., ASC, a Novel 22-kDa Protein, Aggregates during Apoptosis of Human Promyelocytic Leukemia HL-60 Cells, The Journal of Biological Chemistry, 1999, vol. 274, pp. 33835-33838.*
McConnell et al. "TMS1/ASC: The Cancer Connection" (2004) Apoptosis, vol. 9: 5-18.*

International Preliminary Report on Patentability dated Oct. 6, 2010 in PCT Application No. PCT/EP2009/004765.
English Translation of Japanese Office Action for Corresponding Japanese Patent Application No. 2011-509903, dated Jan. 16, 2012.
English Patent Abstract of JP 2006-061002; Publication Date Mar. 9, 2006.
Kubo et al., "Apoptotic Speck Protein-Like, a Highly Homologous Protein to Apoptotic Speck Protein in the Pyrin Domain, Is Silenced by DNA Methylation and Induces Apoptosis in Human Hapatocellular Carcinoma," Cancer Research, vol. 64, pp. 5172-5177, Aug. 2004.
Wang, J; Anhui Medical University, 2008, 43 (1) pp. 46-50.
Zhang et al, "Prognostic Value of Apoptosis-Associated Speck-like Protein Containing a CARD Gene Promoter Methylation in Resectable Non-Small-Cell Lung Cancer," Clinical Lung Cancer, Jul. 2006, pp. 62-65.
Mark Zweig and Gregory Campbell, "Receiver-Operating Characteristic (ROC) Plots: A Fundamental Evaluation Tool in Clinical Medicine," Clinical Chemistry, vol. 39, No. 4, 1993, pp. 561-577.
P. Tijssen, Practice and Theory of Enzyme Immunoassays, 1985, ISBN 0-444-80633-4, pp. 108-121.
P. Tijssen, Practice and Theory of Enzyme Immunoassays, 1985, Chapter 5, Production of Antibodies, pp. 44-78.
Wang; Pulm J, Dec. 2, 2007, Diagnostic value of four serum tumor markers for lung cancer.
Beth McConnell and Paula Vertino, "Activation of a Caspase-9-Mediated Apoptotic pathway by Subcellular Redistribution of the Novel Caspase Recruitment Domain," Cancer Research 60, Nov. 15, 2000, pp. 6243-6247.
Ingo Ruczinski et al, "Logic Regression," Journal of computational and Graphical Statistics, vol. 12, No. 3, 2003, pp. 475-511.
Junya Masumoto et al, "Expression of Apoptosis-Associated Speck-Like Protein Containing a Caspase Recruitment Domain, a Pyrin N-Terminal Homology Domain-Containing Protein, in Normal Human Tissues," The Journal of Histochemistry & Cytochemistry, vol. 49(10: 2001; pp. 1269-1275.
Jerome H. Friedman, "Regularized Discriminant Analysis," Journal of the American Statistical Association, Mar. 1989, vol. 84, No. 405, pp. 165-175.
Jeoffrey J. Levine et al, "Effects of Methylation on Expression of TMS1/ASC in Human Breast Cancer Cells," Oncogene (2003) 22; pp. 3475-3488.
Kerry E. Conway et al, "TMS1, a Novel Proapoptotic Caspase Recruitmemt Domain Protein, Is a Target of Methylation-Induced Gene Silencing in Human Breast Cancers," Cancer Research 60, Nov. 15, 2000, pp. 6236-6242.
International Search Report dated Oct. 9, 2009 in PCT Application No. PCT/EP2009/004765.
Buccheri, Gianfranco and Ferrigno, Domenico, Identifying Patients at Risk of Early Postoperative Recurrence of Lung Cancer: A New Use of the Old CEA Test, Annals in Thoractic Surgery, 2003, pp. 973-980, vol. 75.

(Continued)

*Primary Examiner* — Teresa E Knight
(74) *Attorney, Agent, or Firm* — Dinsmore & Shohl LLP (57) ABSTRACT

The present invention relates to the assessment of lung cancer. It discloses the use of protein ASC in the assessment of lung cancer. It also relates to a method for assessing lung cancer in vitro using a liquid sample, derived from an individual by measuring ASC in the sample. Measurement of ASC can, e.g., be used in the early detection or in the follow-up of patients with lung cancer.

13 Claims, 3 Drawing Sheets

Specification includes a Sequence Listing.

(56) References Cited

OTHER PUBLICATIONS

Duffy, M. J., Clinical Uses of Tumor Markers: A Critical Review, Critical Reviews in Clinical Laboratory Sciences, 2011, pp. 225-262, vol. 38, No. 3.

Fukasawa, Toshio et al., Clinical Evaluation of Serum NSE and CEA in Primary Lung Cancer Patients, Japanese Journal of Cancer and Chemotherapy, May 1986, pp. 1862-1867, vol. 13, No. 5 (English Abstract on p. 1867).

Machida, Emi Ota et al., Hypermethylation of ASC/TMS1 Is a Sputum Marker for Late-Stage Lung Cancer, Cancer Research, Jun. 15, 2006, pp. 6210-6218, vol. 66, No. 12.

Merle, P. et al., Early CYFRA 21-1 variation predicts tumor response to chemotherapy and survival in locally advanced non-small cell lung cancer patients, The International Journal of Biological Markers, 2004, pp. 310-315, vol. 19, No. 4.

Molina, R. et al., Tumor Markers (CEA, CA 125, CYFRA 21-1, SCC and NSE) in Patients with Non-Small Cell Lung Cancer as an Aid in Histological Diagnosis and Prognosis, Tumor Biology, 2003, pp. 209-218, No. 24.

Moriai, Ryosuke et al., A Proapoptotic Caspase Recruitment Domain Protein Gene, TMS1, is Hypermethylated in Human Breast and Gastric Cancers, Anticancer Research, 2002, pp. 4163-4168, vol. 22.

Schneider, Joachim et al., Fuzzy logic-based tumor-marker profiles improved sensitivity in the diagnosis of lung cancer, International Journal of Clinical Oncology, 2002, pp. 145-151, vol. 7.

Schneider, Joachim, Tumor Markers in Detection of Lung Cancer, Advances in Clinical Chemistry, 2006, pp. 1-41, vol. 42.

Shiohara, Masaaki et al., ASC, Which Is Composed of a Pyrin-N-Terminal Homology Domain and a Caspase-Recruitment Domain, Is Up-Regulated by Inflammation and Apoptosis in Human Neutrophils, Blood, 2001, p. 229a, vol. 98.

Virmani, Arvind et al., Aberrant Methylation of TMS1 in Small Cell, Non Small Cell Lung Cancer and Breast Cancer, International Journal of Cancer, 2003, pp. 198-204, vol. 106.

Wagner, Henry, Jr., Postoperative Adjuvant Therapy for Patients With Resected Non-Small Cell Lung Cancer: Still Controversial After all These Years, Chest, 2000, pp. 110S-118S, vol. 117.

Zhang, Zhixue et al., Prognostic Value of Apoptosis-Associated Speck-like Protein Containing a CARD Gene Promoter Methylation in Resectable Non-Small-Cell Lung Cancer, Clinical Lung Cancer, 2006, pp. 62-65, vol. 8, No. 1.

* cited by examiner

SEQUENCE LISTING

<160> NUMBER OF SEQ ID NOS: 2

<210> SEQ ID NO 1
<211> LENGTH: 195
<212> TYPE: PRT
<213> ORGANISM: Homo sapiens

<400> SEQUENCE: 1

```
Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
        195
```

```
<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      extension sequence

<400> SEQUENCE: 2

Met Arg Gly Ser His His His His His His Ile Glu Gly Arg
1               5                   10
```

ASC AS A MARKER FOR LUNG CANCER

RELATED APPLICATIONS

This application is a continuation of PCT/EP2009/004765 filed Jul. 1, 2009 and claims priority to EP 08012070.2 filed Jul. 3, 2008.

SEQUENCE LISTING

The instant application contains a Sequence Listing which has been submitted in ASCII format via EFS-Web and is hereby incorporated by reference in its entirety. Said ASCII copy, created on Dec. 14, 2010, is named 24716US.txt, and is 2,380 bytes in size.

FIELD OF THE INVENTION

The present invention relates to a method aiding in the assessment of pulmonary or lung cancer (=LC) and in particular in the assessment of non-small cell lung carcinoma (NSCLC). It discloses the use of the "apoptosis-associated speck-like protein containing a caspase-associated recruitment domain" (ASC) as a marker of LC, particularly of NSCLC. Furthermore, it especially relates to a method for assessing lung cancer from a liquid sample, derived from an individual by measuring ASC in said sample. Measurement of ASC can, e.g., be used in the early detection of lung cancer or in the surveillance of patients who undergo surgery.

BACKGROUND OF THE INVENTION

Cancer remains a major public health challenge despite progress in detection and therapy. Amongst the various types of cancer, LC is a frequent cancer in the Western world and among the most frequent causes of cancer-related mortality. This is in large part due to the diagnostic gap for early detection of the disease. LC is largely asymptomatic in its early stages. The majority of all lung cancers is detected at a late stage when the disease has already become inoperable.

The majority of LC tumors can be divided into small cell lung carcinoma (SCLC) and non-small cell lung carcinoma (NSCLC). SCLC accounts for about 20-25% of all lung cancer cases. SCLC is an aggressive neuroendocrine type of LC and has a very poor prognosis even if detected in early stages. SCLC is rarely amenable to curative treatment by resection. Because of the speed with which the disease progresses, SCLC is generally categorized using only two stages, i.e. limited and extensive disease, rather than the more complex TNM staging system (see below). About 75-80% of LC cases are grouped into the class of NSCLC including squamous cell carcinoma (carcinoma=CA), adeno CA (comprising the subclasses of acinar CA, papillary CA, bronchoalveolar tumor, solid tumor, and mixed subtypes), and large cell carcinoma (comprising the subclasses of giant cell tumors, clear cell CA, adenosquamous CA, and undifferentiated CA).

NSCLC, if detected at late stages, also has a very poor prognosis. The staging of cancer is the classification of the disease in terms of extent, progression, cell type and tumor grade. It groups cancer patients so that generalizations can be made about prognosis and the choice of therapy.

Today, the TNM system is the most widely used classification system based on the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), edition, 1997 (Sobin, L. H., and Fleming, I. D., TNM 80 (1997) 1803-4).

Surgical resection of the primary tumor is widely accepted as the treatment of choice for early stage NSCLC. With the progression of NSCLC and, more specifically, the transition from stage IIIa (T3N1M0, T1N2M0, T2N2M0, T3N2M0) to IIIb (T4N0M0, T4N1M0, T4N2M0), a significant shift in the physician's approach is precipitated. However, if the cancer is detected during the more early stages (Ia-IIIa; preferably up to stage T3N1M0), the five-year survival rate varies between 35% and 80%. Detection at stage Ia ((T1N0M0); small tumor size, no metastasis) has evidently the best prognosis with a five-year survival of up to 80%.

Surgery is rarely, if ever, used in the management of stage IIIb-IV of NSCLC. Stage IV corresponds to distant metastasis, i.e. spread of the disease beyond the lungs and regional lymph nodes. The five-year survival rate in the later stages III and IV drops to between less than 15% and 1%, respectively.

What is especially important is, that early diagnosis of NSCLC translates to a much better prognosis. Patients diagnosed as early as in stage Ia (T1N0M0), Ib (T2N0M0), IIa (T1N1M0), IIb, (T3N0M0), and IIIa (T3N1M0), if treated properly have an up to 80% chance of survival 5 years after diagnosis. This has to be compared to a 5-years survival rate of less than 1% for patients diagnosed once distant metastases are already present.

In the sense of the present invention early assessment of LC refers to an assessment at a tumor stage of between Ia and IIIa, as defined above.

It is preferred, that LC is assessed at a stage of between Ia and IIIa.

Most lung cancers are detected when they become symptomatic. Current detection methods include chest x-ray, spiral computer tomography, sputum cytology and bronchioscopy. However, there is controversy regarding the suitability of these means for mass screenings.

A number of serum tumor markers for lung cancers are in clinical use. The soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose (2000) TH Books Verlagsgesellschaft, Frankfurt/Main, Germany).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early LC tumor marker that would aid in the reliable cancer detection or provide early prognostic information could lead to a method that would greatly aid in the diagnosis and in the management of this disease. Therefore, an urgent clinical need exists to improve the in vitro assessment of LC. It is especially important to improve the early diagnosis of LC, since for patients diagnosed early on chances of survival are much higher as compared to those diagnosed at a progressed stage of disease. Especially, there is an urgent need for methods for reliable monitoring of a LC treatment, screening individuals for LC and testing for recurrence of lung cancer after LC therapy.

The clinical utility of biochemical markers in lung cancer has recently been reviewed (Duffy, M. J., Critical Reviews in Clinical Laboratory Sciences 38 (2001) 225-262).

CYFRA 21-1 is currently regarded to be the best of the presently known tumor markers for lung cancer. Even though not organ-specific it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While the sensitivity for SCLC at 95% specificity is reported to be 60-87%, the performance of NSE testing for NSCLC is poor (sensitivity of 7-25%). NSE is recommended for therapy surveillance of SCLC.

ProGRP is a tumor marker, useful in the detection and monitoring of SCLC. Increased serum levels are also found in patients with nonmalignant lung/pleural diseases, such as idiopathic pulmonary fibrosis or sarcoidosis. While sensitivity for proGRP in the field of SCLC (at 95% specificity) is reported to be 47-86%, the performance of proGRP testing in the field of NSCLC is poor because the sensitivity is reported as being below 10%.

SCC was originally identified in squamous cell CA of the cervix. The sensitivity of SCC for LC in general is low (18-27%). Therefore, SCC testing is regarded to be not suitable for screening. However, due to a higher sensitivity for squamous cell CA, a preferred use for SCC is therapy surveillance, even though CYFRA 21-1 generally performs better.

With respect to marker profiles and aiming at improved diagnosis of lung cancer, a method was published (Schneider, J. et al. Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%. However in this study, for example the sensitivity of CYFRA 21-1 as a single tumor marker is reported to be at 72% at a specificity of 95%, which is significantly higher than in many other reported studies. Duffy, M. J., in Critical Reviews in Clinical Laboratory Sciences 38 (2001) 225-262 report a sensitivity of between 46% and 61%. This unusual high performance achieved by Schneider et al., raises some doubts and might be due to several facts. Firstly, the collective of control patients seems to be younger than the patients collective, i.e. the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, it has to be expected that the same algorithm applied to a larger, independent, and well balanced validation set will lead to a significantly reduced overall performance.

It was the task of the present invention to investigate whether a biochemical marker can be identified which may be used in assessing LC.

Surprisingly, it has been found that use of the marker ASC (Apoptosis-associated Speck-like protein containing a CARD) can at least partially overcome some of the problems of the markers presently known in the state of the art.

SUMMARY OF THE INVENTION

The present invention relates to a method for assessing lung cancer in vitro comprising measuring in a sample the presence and/or concentration of ASC, and using the measurement result, particularly the concentration determined in the assessment of lung cancer.

In preferred embodiments, the novel marker ASC may be used for monitoring as well as for screening purposes.

When used in patient monitoring the diagnostic method according to the present invention may help to assess tumor load, efficacy of treatment and tumor recurrence in the follow-up of patients. Increased levels of ASC are directly correlated to tumor burden. After chemotherapy a short term (few hours to 14 days) increase in ASC may serve as an indicator of tumor cell death. In the follow-up of patients (from 3 months to 10 years) an increase of ASC can be used as an indicator for tumor recurrence.

In a preferred embodiment the diagnostic method according to the present invention is used for screening purposes. I.e., it is used to assess subjects without a prior diagnosis of LC by measuring the level of ASC and correlating the level measured to the presence or absence of LC.

The present invention is also directed to a method for assessing LC in vitro by biochemical markers, comprising measuring in a sample the presence and/or concentration of ASC and of one or more other marker of LC and using the measurement results, particularly concentrations determined in the assessment of LC. It is preferred that the one or more other marker of LC is selected from the group consisting of CYFRA 21-1, CEA, NSE, proGRP and SCC.

The present invention also relates to the use of a marker panel comprising ASC and one or more additional marker in the assessment of LC, wherein a preferred additional marker is selected from the group consisting of CYFRA 21-1, CEA, NSE, proGRP and SCC.

The present invention, in a preferred embodiment, also relates to the use of a marker panel comprising at least ASC and CYFRA 21-1 in the assessment of LC.

The present invention also relates to the use of a marker panel comprising at least ASC and CEA in the assessment of LC.

The present invention also relates to the use of a marker panel comprising at least ASC and SCC in the assessment of LC.

The present invention further relates to a kit for performing the method according to the present invention comprising at least the reagents required to specifically measure ASC and optionally auxiliary reagents for performing the measurement.

The present invention also provides a kit for performing the method according to the present invention comprising at least the reagents required to specifically measure ASC and CYFRA 21-1, respectively, and optionally auxiliary reagents for performing the measurement.

The present invention also provides a kit for performing the method according to the present invention comprising at least the reagents required to specifically measure ASC and CEA, respectively, and optionally auxiliary reagents for performing the measurement.

The present invention also provides a kit for performing the method according to the present invention comprising at least the reagents required to specifically measure ASC and SCC, respectively, and optionally auxiliary reagents for performing the measurement.

In a preferred embodiment the present invention relates to a method for assessing lung cancer in vitro comprising measuring in a sample the presence and/or concentration of a) ASC, and b) optionally one or more other marker of lung cancer, and c) using the measurement results, particularly the concentrations determined in step (a) and optionally step (b) in the assessment of lung cancer.

DETAILED DESCRIPTION OF THE INVENTION

The term "measurement" comprises a qualitative or a quantitative measurement of ASC in a sample. In a preferred embodiment the measurement is a qualitative or semi-quantitative measurement, i.e. it is determined whether ASC is present or absent or it is determined whether the concentration of ASC is above or below a cut-off value. As the skilled artisan will appreciate, in a Yes-(presence) or No-(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. Presence of a value above the cut-off value can for example be indicative for the presence of lung cancer. In a further preferred embodiment the measurement is a quantitative measurement. In this embodiment the concentration of ASC is correlated to an underlying diagnostic question like e.g. stage of disease, disease progression, or response to therapy.

The "apoptosis-associated speck-like protein containing a caspase-associated recruitment domain" (ASC), also known as "target of methylation-induced silencing 1" (TMS1) (Swiss-PROT: Q9ULZ3) is characterized by the sequence given in SEQ ID NO:1. ASC has a theoretical molecular weight of 21,627 Da and a theoretical isoelectric point of pH 6.29.

Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family.

By immunoscreening a promyelocytic cell line, Masumoto et al. isolated a cDNA encoding ASC. The deduced 195-amino acid protein contains an N-terminal pyrin-like domain (PYD) and an 87-residue C-terminal CARD. Western blot analysis showed expression of a 22-kDa protein and indicated that ASC may have proapoptotic activity by increasing the susceptibility of leukemia cell lines to apoptotic stimuli by anticancer drugs (Masumoto, J, et al., J. Biol. Chem. 274 (1999) 33835-33838).

Methylation-sensitive restriction PCR and methylation-specific PCR (MSP) analyses by Conway et al. indicated that silencing of ASC correlates with hypermethylation of the CpG island surrounding exon1 and that overexpression of DNMT1 (DNA cytosine-5-methyltransferase-1) promotes hypermethylation and silencing of ASC. Breast cancer cell lines, but not normal breast tissue, exhibited complete methylation of ASC and expressed no ASC message. Expression of ASC in breast cancer cell lines inhibited growth and reduced the number of surviving colonies. Conway et al. concluded that ASC functions in the promotion of caspase-dependent apoptosis and that overexpression of ASC inhibits the growth of breast cancer cells (Conway, K. E., et al., Cancer Research 60 (2000) 6236-6242).

McConnell and Vertino showed that inducible expression of ASC inhibits cellular proliferation and induces DNA fragmentation that can be blocked by caspase inhibitor. Immunofluorescence microscopy demonstrated that induction of apoptosis causes a CARD-dependent shift from diffuse cytoplasmic expression to spherical perinuclear aggregates (McConnell, B. B., and Vertino, P. M., Cancer Research 60 (2000) 6243-6247). Moriani et al. observed methylation of ASC gene not only in breast cancer cells but also in gastric cancer. They suggested a direct role for aberrant methylation of the ASC gene in the progression of breast and gastric cancer involving down-regulation of the proapoptotic ASC gene (Moriani, R., et al., Anticancer Research 22 (2002) 4163-8).

Conway et al. examined primary breast tissues for TMS1 methylation and compared the results to methylation in healthy tissues (Conway K. E., et al., Cancer Research 60 (2000) 6236-6242). Levine et al. found that ASC silencing was not correlated with methylation of specific CpG sites, but rather was associated with dense methylation of ASC CpG island. Breast tumor cell lines containing exclusively methylated ASC copies do not express ASC, while in partially methylated cell lines the levels of ASC expression are directly related to the percentage of methylated ASC allels present in the cell population (Levine, J. J., et al., Oncogene 22 (2003) 3475-3488).

Virmani et al. examined the methylation status of ASC in lung cancer and breast cancer tissue. They found that aberrant methylation of ASC was present in 46% of breast cancer cell lines and in 32% of breast tumor tissue. Methylation was rare in non-malignant breast tissue (7%) (Virmani, A., et al., Int. J. Cancer 106 (2003) 198-204).

Zhang et al. describe ASC as a tumor suppressor gene that is frequently inactivated by de novo promoter methylation in non-small-cell lung cancer (NSCLC). The authors conclude that ASC promoter hypermethylation is a common event in patients with primary NSCLC which is associated with inferior survival (Zhang, Z., et al., Clin Lung Cancer. 8(1) (2006) 62-65).

Shiohara et al. found out that up-regulation of ASC is closely associated with inflammation and apoptosis in human neutrophils (Shiohara, M., et al., Blood 98 (2001) 229a).

Masumoto et al. observed that high levels of ASC are abundantly expressed in epithelial cells and leucocytes (Masumoto, J., et al., Journal of Histochemistry and Cytochemistry 49 (2001) 1269-1275).

WO 2006/066915 A1 and WO 2006/066917 A2 describe ASC as a tumor marker indicative for colorectal cancer.

WO 2005/040806 A2 discloses that ASC is a suitable marker for diagnosing breast cancer.

In WO 2008/063655 a method is described for identifying metastases and particularly micrometastases by detecting nucleic acid hypermethylation and the silencing resulting therefrom of one or more genes in a sample. As gene, among others, ASC is mentioned.

WO 01/29235 discloses methods for diagnosing cancer, comprising the determination of the methylisation level of the ASC (TMS1)-gene or the measurement of the TMS1 expression profile in a sample as for example blood. The latter comprising the measurement of the TMS1 polypeptide, whereby a low concentration of TMS1 results from the presence of cancer disease.

Machida et al., Cancer Research, vol. 66, no. 12, June 2006 (2006-06), pages 6210-6218, teach an association of a hypermethylation of the ASC gene and a reduced ASC protein level with the occurrence of lung cancer. An ASC hypermethylation thereby in particular correlates with progressed tumor stages.

Interestingly, none of the above documents suggests that a determination of ASC in tissue extracts and in body fluids would allow assessment of lung cancer. Surprisingly, it was found in the present invention that a determination of the presence and/or amount of ASC in a tissue lysate sample and/or body fluid allows the assessment of lung cancer. Further, the inventors found out that a reliable assessment of LC is possible by measuring ASC within a liquid sample from an individual, i.e. no tissue and no biopsy sample is required in diagnosis of LC when using protein ASC as marker. Even more surprisingly it was found that an increased level of ASC as measured from a bodily fluid of an individual is associated with lung cancer.

As obvious to the skilled artisan, the present invention shall not be construed to be limited to the full-length protein ASC of SEQ ID NO:1. Physiological or artificial fragments of ASC, secondary modifications of ASC, as well as allelic variants of ASC are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO:1. Such fragment may advantageously be used for generation of antibodies or as a standard in an immunoassay. More preferred the artificial fragment comprises at least two epitopes of interest appropriate for setting up a sandwich immunoassay.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker. The term "at least" is used to indicate that optionally one or more further objects may be present. By way of example, a marker panel comprising at least (the markers) ASC and CYFRA 21-1 may optionally comprise one or more other marker.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. In one embodiment examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (=PI) or molecular weight (=MW), or both e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Preferred posttranslational modifications are glycosylation, acylation, and/or phosphorylation.

Preferably the marker ASC is specifically measured from a sample by use of a specific binding agent.

A specific binding agent is, e.g., a receptor for ASC, a lectin binding to ASC or an antibody to ASC. A specific binding agent has at least an affinity of $10^7$ l/mol for its corresponding target molecule. The specific binding agent preferably has an affinity of $10^8$ l/mol or also preferred of $10^9$ l/mol for its target molecule. As the skilled artisan will appreciate the term specific is used to indicate that other biomolecules present in the sample do not significantly bind to the binding agent specific for ASC. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity.

A specific binding agent preferably is an antibody reactive with ASC. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108-115).

For the achievements as disclosed in the present invention polyclonal antibodies raised in rabbits may be used. However, clearly also polyclonal antibodies from different species, e.g., rats or guinea pigs, as well as monoclonal antibodies can also be used. Since monoclonal antibodies can be produced in any amount required with constant properties, they represent ideal tools in development of an assay for clinical routine. The generation and the use of monoclonal antibodies to ASC in a method according to the present invention, respectively, represent yet other preferred embodiments.

As the skilled artisan will appreciate now, that ASC has been identified as a marker which is useful in the assessment of lung cancer, various immunodiagnostic procedures may be used to reach a result comparable to the achievements of the present invention. For example, alternative strategies to generate antibodies may be used. Such strategies comprise amongst others the use of synthetic peptides, representing an epitope of ASC for immunization. Alternatively, DNA immunization also known as DNA vaccination may be used.

For measurement the sample obtained from an individual is incubated with the specific binding agent for ASC under conditions appropriate for formation of a binding agent ASC-complex. Such conditions need not be specified, since the skilled artisan without any inventive effort can easily identify such appropriate incubation conditions. The amount of binding agent ASC-complex is measured and used in the assessment of lung cancer. As the skilled artisan will appreciate there are numerous methods to measure the amount of the specific binding agent ASC-complex all described in detail in relevant textbooks (cf., e.g., Tijssen P., supra, or Diamandis, E. P. and Christopoulos, T. K. (eds.), Immunoassay, Academic Press, Boston (1996)).

Preferably ASC is detected in a sandwich type assay format. In such assay a first specific binding agent is used to capture ASC on the one side and a second specific binding agent, which is labeled to be directly or indirectly detectable, is used on the other side.

In a preferred embodiment, measurement of ASC in a sample is carried out by using a sandwich immunoassay, wherein Streptavidin-coated microtiter plates are used. A biotinylated polyclonal antibody to ASC is used as a capturing antibody and a digoxigenylated polyclonal antibody to ASC is used as the second specific binding partner in this sandwich assay. The sandwich complex formed is finally visualized by an anti-digoxigenin horseradish peroxidase conjugate and an appropriate peroxidase substrate.

As mentioned above, ASC can be measured from a liquid sample obtained from an individual sample. No tissue and no biopsy sample is required to apply the marker ASC in the diagnosis of LC.

In a preferred embodiment the method according to the present invention is practiced with serum as liquid sample material.

In a further preferred embodiment the method according to the present invention is practiced with plasma as liquid sample material.

In a further preferred embodiment the method according to the present invention is practiced with whole blood as liquid sample material.

In a further preferred embodiment the method according to the present invention is practiced with nipple aspirate fluid as liquid sample material:

A "marker of lung cancer" in the sense of the present invention is any marker that if combined with the marker ASC adds relevant information in the assessment of LC. The information is considered relevant or of additive value if at a given specificity the sensitivity, or if at a given sensitivity the specificity, respectively, for the assessment of LC can be improved by including said marker into a marker combination already comprising the marker ASC. Preferably the improvement in sensitivity or specificity, respectively, is statistically significant at a level of significance of p=0.05, 0.02, 0.01 or lower. Preferably, the one or more other marker of LC is selected from the group consisting of CYFRA 21-1, CEA, NSE, proGRP and SCC.

The term "sample" as used herein refers to a biological sample obtained for the purpose of evaluation in vitro. In the methods of the present invention, the sample or patient sample preferably may comprise any body fluid or a tissue extract. Preferred test samples include blood, serum, plasma, sputum and bronchial lavage. Preferred samples are whole blood, serum, plasma, bronchial lavage or sputum, with plasma or serum being most preferred.

The term "assessing lung cancer" is used to indicate that the method according to the present invention will (alone or together with other markers or variables, e.g., the criteria set forth by the UICC (see above)) e.g., aid the physician to establish or confirm the absence or presence of LC or aid the physician in the prognosis, the detection of recurrence (follow-up of patients after surgery), screening and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

In a preferred embodiment the present invention relates to a method for assessing LC in vitro by biochemical markers, comprising measuring in a sample the concentration of ASC and using the concentration determined in the assessment of LC.

The inventors of the present invention have surprisingly been able to detect the marker protein ASC in a significant percentage of samples derived from patients with LC. Even more surprising they have been able to demonstrate that the presence and/or concentration of ASC in such sample obtained from an individual can be used in the assessment of lung cancer.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for LC. As the skilled artisan will appreciate, no biochemical marker is diagnostic with 100% specificity and at the same time 100% sensitivity for a given multifactorial disease, for example for LC. Rather, biochemical markers, e.g., CYFRA 21-1, CEA, NSE, proGRP, SCC, or as shown here ASC can be used to assess with a certain likelihood or predictive value e.g., the presence, absence, or the severity of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently, e.g., using an individual cut-off for each marker, or they are combined for interpretation.

In a further preferred embodiment the assessment of LC according to the present invention is performed in a method comprising measuring in a sample the presence and/or concentration of a) ASC, and b) one or more other marker of lung cancer, and c) using the measurement result, e.g. the concentrations determined in step (a) and step (b), respectively, in the assessment of lung cancer.

In the assessment of LC the marker ASC will be of advantage in one or more of the following aspects: screening; diagnostic aid; prognosis; monitoring of therapy such as chemotherapy, radiotherapy, and immunotherapy.

Screening:

Screening is defined as the systematic application of a test to identify individuals e.g. at risk individuals, for indicators of a disease, e.g., the presence of lung cancer. Preferably the screening population is composed of individuals known to be at higher than average risk of lung cancer, like smokers, ex-smokers, and uranium-, quartz- or asbestos-exposed workers.

In one preferred embodiment sputum is used as a sample in the screening for lung cancer.

For many diseases, no single biochemical marker in the circulation will ever meet the sensitivity and specificity criteria required for screening purposes. This appears to be also true for lung cancer. It has to be expected that a marker panel comprising a plurality of markers will have to be used in LC screening. The data established in the present invention indicate that the marker ASC will form an integral part of a marker panel appropriate for screening purposes. The present invention therefore relates to the use of ASC as one marker of a LC marker panel, i.e. a marker panel comprising APEX and one or more additional marker for LC screening purposes. Preferred additional markers are selected from the group consisting of CYFRA 21-1, CEA, NSE, proGRP and SCC.

Diagnostic Aid:

Markers may either aid the differential diagnosis of benign vs. malignant disease in a particular organ, help to distinguish between different histological types of a tumor, or to establish baseline marker values before surgery.

Today, important methods used in the detection of lung cancer are radiology and/or computed tomography (CT) scans. Small nodules, i.e. small regions of suspect tissue can be visualized by these methods. However, many of these nodules—more than 90% with CT—represent benign tissues changes, and only a minority of nodules represents cancerous tissue. Use of the marker ASC may aid in the differentiation of benign versus malign nodules.

In a preferred embodiment the marker ASC is used in an immunohistological method in order to establish or confirm different histological types of LC.

Since ASC as a single marker might be superior to other LC markers like CEA or NSE it has to be expected that ASC will be used as a diagnostic aid, especially by establishing a baseline value before surgery. The present invention thus also relates to the use of ASC for establishing a baseline value before surgery for LC.

Prognosis:

Prognostic indicators can be defined as clinical, pathological, or biochemical features of cancer patients and their tumors that predict with a certain likelihood the disease outcome. Their main use is to help to rationally plan patient management, i.e. to avoid undertreatment of aggressive disease and overtreatment of indolent disease, respectively. Molina R. et al., Tumor Biol. (2003) 24:209-218 evaluated the prognostic value of CEA, CA 125, CYFRA 21-1, SSC and NSE in NSCLC. In their study abnormal serum levels of the markers NSE, CEA, and LDH (lactate dehydrogenase) appeared to indicate shorter survival.

As ASC alone significantly contributes to the differentiation of LC patients from healthy controls, it has to be expected that it will aid in assessing the prognosis of patients suffering from LC. The level of preoperative ASC will most likely be combined with one or more other marker for LC and/or the TNM staging system. In a preferred embodiment ASC is used in the prognosis of patients with LC.

Monitoring of Chemotherapy:

Merle, P. et al., Int. J. of Biological Markers (2004) 19:310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients. In addition, reports have described the use of CEA in monitoring the treatment of patients with LC (Fukasawa T. et al., Cancer & Chemotherapy (1986) 13:1862-1867). Most of these studies were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that ASC will be at least as good a marker for monitoring of chemotherapy as CYFRA 21-1 or CEA, respectively. The present invention therefore also relates to the use of ASC in the monitoring of LC patients under chemotherapy.

Follow-Up:

A large portion of LC patients who undergo surgical resection aimed at complete removal of cancerous tissue later develop recurrent or metastatic disease (Wagner, H., Chest (2000) 117:110-118; Buccheri, G. et al., Ann. Thorac. Surg. (2003) 75:973-980). Most of these relapses occur within the first 2-3 years after surgery. Since recurrent/ metastatic disease is invariably fatal if detected too late, considerable research has focused on LC relapse at an early and thus potentially treatable stage.

Consequently, many LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G. et al., Ann. Thorac. Surg. (2003) 75:973-980). Thus, the follow-up of patients with LC after surgery is one of the most important fields of use for an appropriate biochemical marker. Due to the high sensitivity of ASC in the LC patients investigated it is likely that ASC alone or in combination with one or more other marker will be of great help in the follow-up of LC patients, especially in LC patients after surgery. The use of a marker panel comprising ASC and one or more other marker of LC in the follow-up of LC patients represents a further preferred embodiment of the present invention.

The present invention in a preferred embodiment relates to the use of ASC in the diagnostic field of LC or in the assessment of LC, respectively.

In yet a further preferred embodiment the present invention relates to the use of ASC as a marker molecule for lung cancer in combination with one or more marker molecules for lung cancer in the assessment of lung cancer from a liquid sample obtained from an individual. Preferred selected other LC markers with which the measurement of ASC may be combined are CYFRA 21-1, CEA, NSE, proGRP, and/or SCC. Yet further preferred the marker panel used in the assessment of LC comprises ASC and at least one other marker molecule selected from the group consisting of CYFRA 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g. the case when diagnosing an infectious disease, like AIDS.

Frequently, however, the combination of markers is evaluated. Preferably the values measured for markers of a marker panel, e.g. for ASC and CYFRA 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g. to the absence or presence of LC is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al, J. of Computational and Graphical Statistics, 12 (2003) 475-511; Friedman, J. H., J. of the American Statistical Association 84 (1989) 165-175; Hastie, Trevor, Tibshirani, Robert, Friedman, Jerome, The Elements of Statistical Learning, Springer Series in Statistics, 2001; Breiman, L., Friedman, J. H., Olshen, R. A., Stone, C. J. (1984) Classification and regression trees, California. Wadsworth; Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g. diseased from healthy. In this type of analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter e.g. is the so-called "total error" or alternatively the "area under the curve=AUC". The most common global measure is the area under the ROC plot. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In a preferred embodiment the present invention relates to a method for improving the diagnostic accuracy for LC versus healthy controls by measuring in a sample the concentration of at least ASC and CYFRA 21-1, and optionally of CEA, proGRP, NSE, and/or SCC, respectively and correlating the concentrations determined to the presence or absence of LC, the improvement resulting in more patients being correctly classified as suffering from LC versus healthy controls as compared to a classification based on any single marker investigated alone.

In a preferred method according to the present invention at least the concentration of the biomarkers ASC and CYFRA 21-1, respectively, is determined and the marker combination is used in the assessment of LC.

In a further preferred method according to the present invention at least the concentration of the biomarkers ASC and CEA, respectively, is determined and the marker combination is used in the assessment of LC.

In a further preferred method according to the present invention at least the concentration of the biomarkers ASC, CYFRA 21-1, and CEA, respectively, is determined and the marker combination is used in the assessment of LC.

In a further preferred method according to the present invention at least the concentration of the biomarkers ASC, CYFRA 21-1, and proGRP, respectively, is determined and the marker combination is used in the assessment of LC.

In yet a further preferred method according to the present invention at least the concentration of the biomarkers ASC, CYFRA 21-1, and SCC, respectively, is determined and the marker combination is used in the assessment of LC.

The following examples and the figure are provided to aid the understanding of the present invention, the true scope of which is set forth in the appended claims. It is understood that modifications can be made in the procedures set forth without departing from the spirit of the invention.

Example 1

Identification of ASC as a Marker for Lung Cancer
Sample Preparation for LC-ESI-MSMS-Analysis:

The protein concentration of the soluble protein fraction in a tissue sample is determined using Bio-Rad protein Assay® (Cat. No. 500-0006; Bio-Rad Laboratories GmbH, München, Germany) following the instructions of the supplier's manual. To a volume corresponding to 200 µg or protein 4 ml reduction buffer (9 M urea, 2 mM DTT, 100 mM $KH_2PO_4$, NaOH pH 8.2) is added and incubated for 1 hour. This solution is concentrated to 50 µl in an Amicon® Ultra device (Millipore GmbH, Schwalbach, Germany), and for alkylation transferred into 0.5 ml sample buffer (9 M urea, 4 mM iodoacetamide, 100 mM $KH_2PO_4$, NaOH pH 8.2) and incubated for 6 hours. After alkylation the solution is concentrated in an Amicon® Ultra device to 50 µl and 0.5 ml 9 M urea 10 mM $KH_2PO_4$, NaOH pH 8.2, are added and the solution is again concentrated to 50 This procedure is repeated twice. Subsequently the final 50 µl are diluted to 990 µl with 4 µg trypsin (Proteomics grade, Roche Diagnostics GmbH, Mannheim, Germany) in water and digested over night.

LC-ESI-MSMS-Analysis:

The tryptic digest (100 µl) is separated by two-dimensional HPLC (MudPIT) on a Nano-LC system (Ultimate, Famos, Switchos; LC Packings, Idstein, Germany). The separation is performed with self packed two-dimensional columns (Fused silica: PicoFrit 75 µm, New Objective; RP: ProntoSil 120-5-C18 AQ+, Bischoff; SCX: Partisil 10, Whatman). 11 SCX fractions are generated by step elution with successively increasing amounts of $NH_4Ac$ (0 to 1500 mM). They are further separated on the RP part of the column and online analyzed using data dependent scans with an ESI-MS ion trap (LCQ deca XP; Thermo Electron, Massachusetts, USA; see Table 1 for parameters). For each sample three runs are performed. The raw data are processed with a non-commercial Roche own data managing system using Sequest as base algorithm (Parameters see Tab. 1). The resulting lists of identified peptides and proteins from replicate runs where combined.

The protein ASC is identified by aid of the sequences identified and given in Tab. 1.

Detection of ASC as a Marker for Lung Cancer:

For each patient the identified proteins and the number of corresponding peptides from the tumor sample are compared to the accordant results from adjacent normal tissue. By this means, protein ASC is found to be specifically present or to be strongly abundant in tumor tissue and not to be detectable or to be barely detectable in healthy control tissue.

The protein ASC is strongly over-represented in tumor tissue from patients suffering from lung cancer. The following peptide sequences of the protein ASC are identified by database search form $LCQ-MS^2$-data in tumor tissue:

The following sequences derived from ASC are identified using the above described method.

TABLE 1

Sequences identified by ESI-MSMS

| Sequence | Stretch of amino acid from ASC |
|---|---|
| DAILDALENLTAEELK | 6-21 of SEQ ID NO: 1 |
| DAILDALENLTAEELKK | 6-22 of SEQ ID NO: 1 |
| LVSFYLETYGAELTANVLR | 56-74 of SEQ ID NO: 1 |
| VTNVEWLLDALYGK | 126-139 of SEQ ID NO: 1 |
| VLTDEQYQAVR | 140-150 of SEQ ID NO: 1 |
| KLFSFTPAWNWTCK | 161-174 of SEQ ID NO: 1 |
| DLLLQALR | 175-182 of SEQ ID NO: 1 |
| ESQSYLVEDLER | 183-194 of SEQ ID NO: 1 |

ASC could be identified in tumor tissue lysate samples from 5 of 8 patients with lung adenocarcinoma. In normal tissue lysates ASC could not be identified.

Example 2

Generation of Antibodies to the Lung Cancer Marker Protein ASC

Polyclonal antibody to the lung cancer marker protein ASC is generated for further use of the antibody in the measurement of serum and plasma and blood levels of ASC by immunodetection assays, e.g. Western Blotting and ELISA.

Recombinant Protein Expression in E. coli:

In order to generate antibodies against ASC, the recombinant antigen is produced in E. coli: Therefore, the ASC coding region is PCR amplified from the full-length cDNA clone IRAT p970H075D obtained from the German Resource Center for Genome Research (RZPD, Berlin, Germany) using suitable forward and reverse primers.

The forward primer features (besides the EcoRI cloning and ribosomal binding sites) oligonucleotides coding for an N-terminal MRGSHHHHHHIEGR peptide extension (SEQ ID NO: 2) introduced in-frame to the ASC polypeptide. The EcoRI/BamHI digested PCR fragment is ligated into the corresponding pQE-30 (Qiagen, Hilden, Germany) vector fragment which is subsequently transformed into E. coli XL1-blue competent cells. After sequence analysis, the plasmid is transformed into E. coli BL21 competent cells for expression under the IPTG—inducible T5 promoter of the pQE vector series following the manufacturer's instructions.

For purification of the MRGSHHHHHHIEGR (SEQ ID NO: 2)-ASC fusion protein, 1 l of an over-night induced bacterial culture is pelleted by centrifugation and the cell pellet is resuspended in 20 mM sodium-phosphate buffer, 500 mM sodium chloride, pH 7.4 containing 1 mg/ml lysozyme and Complete™ EDTA-free protease inhibitor tablets. The cells are disrupted by ultrasonication and insoluble material is pelleted by centrifugation and the supernatant is applied to Ni-nitrilotriacetic acid (Ni-NTA) metal-affinity chromatography: The column is washed with several bed volumes of lysis buffer followed by washes with 20 mM sodium-phosphate buffer, 500 mM sodium chloride, 20 mM imidazol, pH 7.4. Finally, bound antigen is eluted with an imidazol gradient from 20 to 500 mM in 20 mM sodium-phosphate buffer, 500 mM sodium chloride, pH 7.4 and stored in 75 mM HEPES-buffer, pH 7.5, 100 mM sodium chloride, 1 mM EDTA, 6.5% sucrose at 4° C.

Generation of Polyclonal Antibodies:

a) Immunization

For immunization, a fresh emulsion of the protein solution (100 µg/ml protein ASC) and complete Freund's adjuvant at the ratio of 1:1 is prepared. Each rabbit is immunized with 1 ml of the emulsion at days 1, 7, 14 and 30, 60 and 90. Blood is drawn and resulting anti-ASC serum is used as described hereinbelow.

b) Purification of IgG (Immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13 000×g, 30 min, 4° C.), the pellet discarded and the supernatant collected. The pH of the supernatant is adjusted to 7.5 by the addition of 2 M Tris-base.

The immunoglobulin in the supernatant is precipitated under vigorous stirring by the drop-wise addition of a 4 M ammonium sulfate solution to a final concentration of 2 M. The precipitated immunoglobulins are collected by centrifugation (8000×g, 15 min, 4° C.).

The supernatant is discarded. The pellet is dissolved in 10 mM NaH$_2$PO$_4$/NaOH, pH 7.5, 30 mM NaCl and exhaustively dialyzed. The dialysate is centrifuged (13 000×g, 15 min, 4° C.) and filtered (0.2 µm).

c) Biotinylation of Polyclonal Rabbit IgG:

Polyclonal rabbit IgG is brought to 10 mg/ml in 10 mM NaH$_2$PO$_4$/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on Superdex 200 (10 mM NaH$_2$PO$_{4 1}$NaOH, pH 7.5, 30 mM NaCl). The fractions containing biotinylated IgG are collected.

d) Immunosorption of Polyclonal Rabbit IgG:

For the ASC immunosorber 10 mg purified recombinant ASC is coupled to 1 ml CNBr-activated Sepharose™ 4B (GE Healthcare, Germany Catalog No. 17-04-30-01) according to the manufacturer's protocol. This affinity column is loaded with 100 mg polyclonal rabbit IgG in PBS, 0.05 Tween 20 followed by washes with a) PBS, b) 0.5 M sodium chloride, 0.05% Tween 20, c) 30 mM sodium chloride. The bound fraction is eluted with 0.5 M glycine, 150 mM sodium chloride adjusted to pH 2.1 with hydrochloric acid and immediately brought to a neutral pH by the addition of 1 M Tris-base. The eluate is concentrated to 10 mg/ml and chromatographed on a TSK-Gel® G3000SW gelfiltration column (Sigma-Aldrich, Germany, catalogue No. 815103) in PBS. The fractions containing IgG monomers are collected.

Example 3

ELISA for the Measurement of ASC in Human Serum and Plasma Samples

For detection of ASC in human serum or plasma, a sandwich ELISA is developed. For capture of the antigen, anti-ASC polyclonal antibody (see Example 2) is immunosorbed and for detection of the antigen anti-ASC polyclonal antibody is conjugated with biotin.

96-well microtiter plates are incubated with 100 µl immunosorbed anti-ASC polyclonal antibody for 60 min at 5 µg/ml in 150 mM disodium carbonate, 350 mM sodium hydrogen carbonate. Subsequently plates are washed three times with PBS, 0.05% Tween 20. Wells are then incubated for 2 h with either a serial dilution of the recombinant protein (see Example 2) as standard antigen or with diluted plasma samples from patients together with 5 µg/ml biotinylated anti-ASC polyclonal antibody. Incubation was in 10 mM phosphate, pH 7.4, 1% BSA, 0.9% NaCl and 0.1% Tween 20. Thereafter, plates are washed three times to remove unbound components. In a next step, wells are incubated with 20 mU/ml anti-biotin-POD conjugate for 60 min in 10 mM phosphate, pH 7.4, 1% BSA, 0.9% NaCl and 0.1% Tween 20. Plates are subsequently washed three times with the same buffer. For detection of bound antigen-antibody complexes, wells are incubated with 100 µl ABTS solution (Roche Diagnostics GmbH, Mannheim, Germany, Catalog No. 11685767) and OD is measured after 30-60 min at 405 nm with an ELISA reader.

Example 4

ASC in Epithelial Lining Fluid (ELF)—Bronchoscopic Microsampling

Bronchoscopic microsampling (BMS) offers the possibility to collect epithelial lining fluid (ELF) near small pulmonary nodules in a largely non-invasive manner. Subsequently, it is possible to measure concentrations of tumor markers in ELF in order to identify a malignant nodule.

The BMS probe (Olympus Medical Systems Corp. Tokyo, Japan, Cat.-No.: BC-402C) is inserted into the lungs through the bronchoscope and consists of an outer polyethylene sheath and an inner cotton probe attached to a stainless steel guide. The inner probe is advanced to the proximity of the nodule and BMS is performed for a few seconds. Afterwards, the inner probe is withdrawn into the outer sheath and both devices are withdrawn simultaneously. The cotton tip is cut off and directly frozen at −80° C. For the determination, ELF is eluted from the cotton tip and can be analyzed subsequently. The concentration of ASC is determined in ELF with the ELISA as described in Example 3.

Example 5

ASC as a Serum Marker for Lung Cancer
Study Population
Study 1

Samples derived from 60 well-characterized NSCLC patients (30 adeno-CA, 30 squamous cell CA) with the UICC classification given in Table 2 are used.

TABLE 2

Study population

| Stage according to UICC | Number of samples |
|---|---|
| UICC I/II | 24 |
| UICC III | 17 |
| UICC IV | 19 |
| obviously healthy blood donors | 30 |
| apparently healthy smokers | 30 |

The level of ASC in the LC samples of Table 2 is evaluated in comparison to 60 control samples obtained from 30 obviously healthy individuals and 30 apparently healthy smokers without any known malignant lung disease (=control cohort).

The level of ASC in the LC samples of Table 2 is increased as compared to the level of ASC in control samples.

Figure 1:
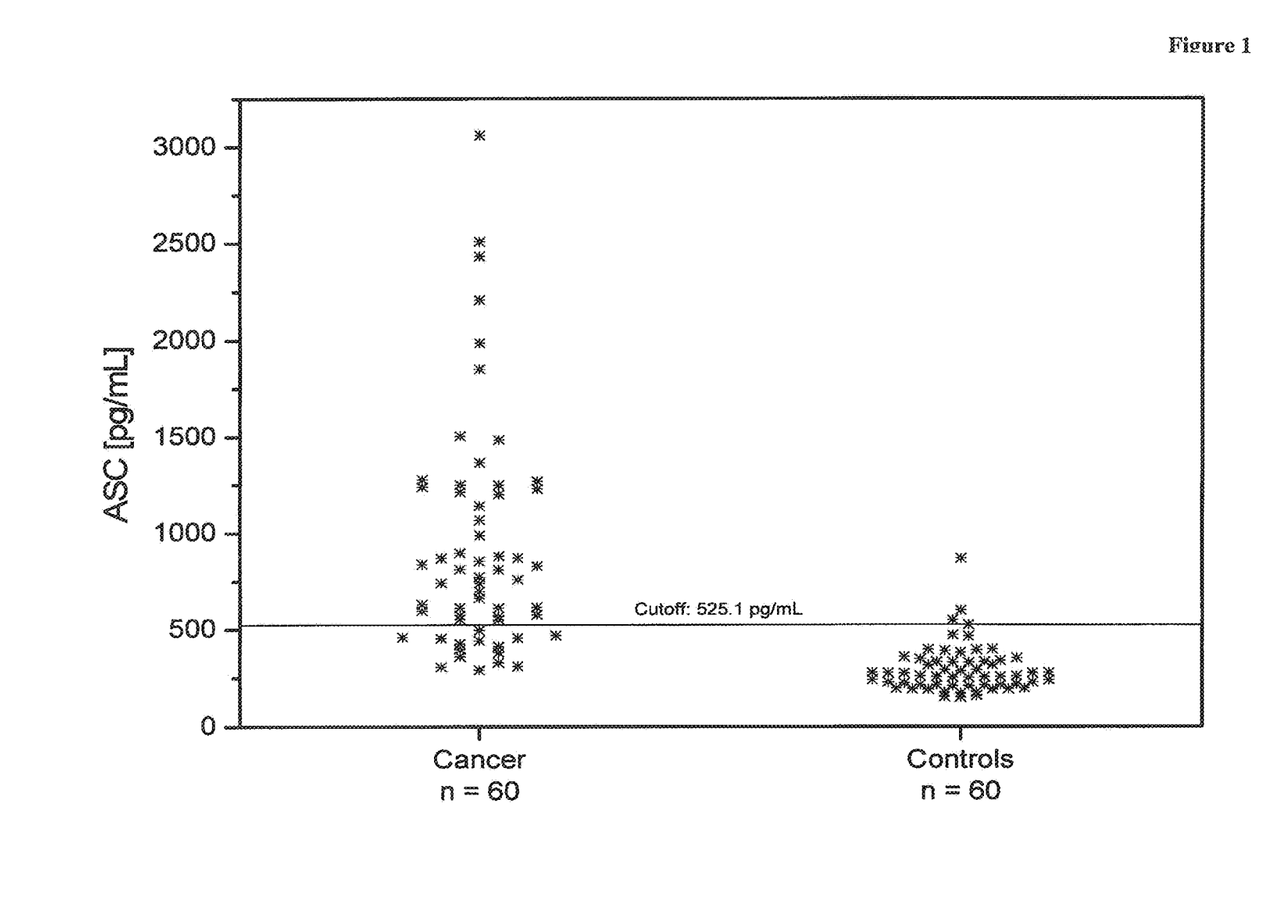
FIG. 1 is a diagram exhibiting correlation of ASC concentration with occurrence of lung cancer. A cut-off value of 525.1 pg/ml is significant for presence of LC. Measurement of ASC was performed on 60 samples obtained from patients with LC ("Cancer") and on 60 control samples obtained from 30 obviously healthy individuals and 30 apparently healthy smokers.
Figure 2:
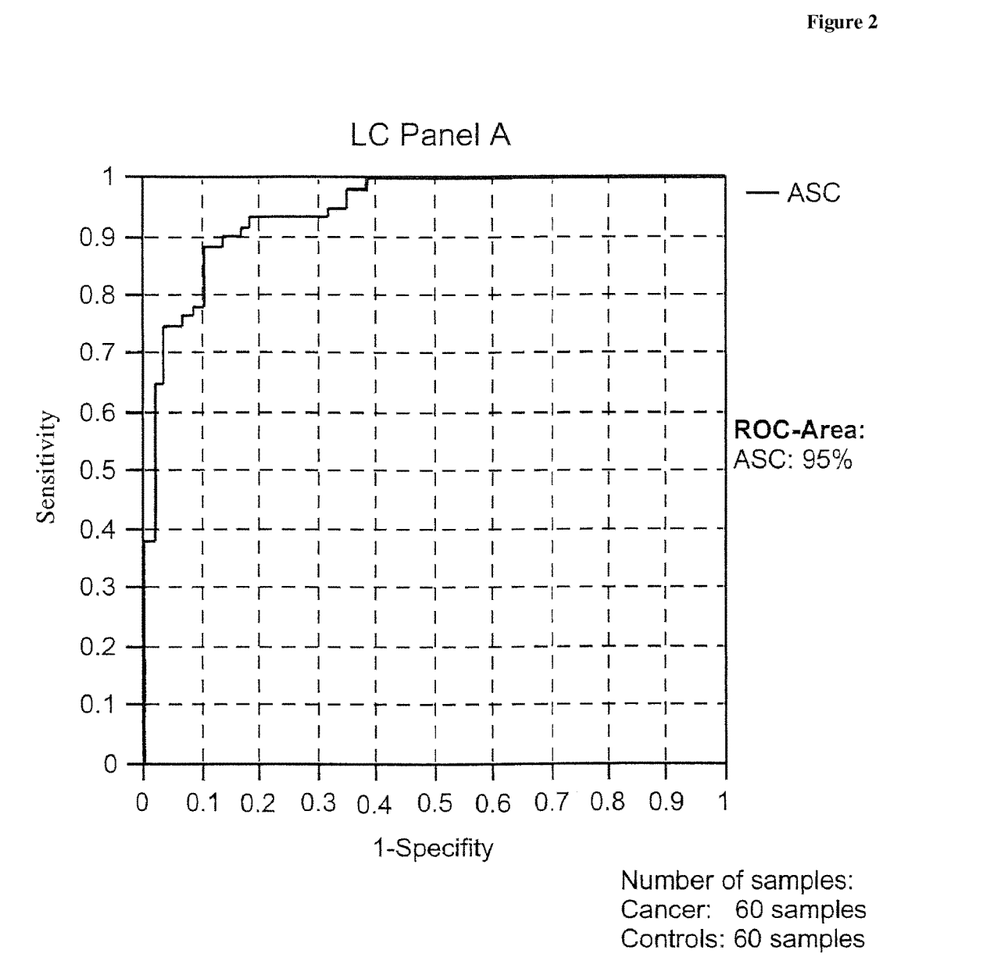
FIG. 2 shows a plot of the receiver operator characteristics (ROC) for the assessment of 60 samples obtained from patients with LC as compared to 60 control samples obtained from 30 obviously healthy individuals and 30 apparently healthy smokers.

ROC-analysis is performed according to Zweig, M. H., and Campbell, supra. Discriminatory power for differentiating patients in the LC group from healthy individuals as measured by the area under the curve is found to be 92% for LC vs. healthy controls (FIGS. 1 and 2).

At 95% specificity the sensitivity of all LC samples was 70%, for adenocarcinomas 67% and for squamous cell carcinoma 73% respectively.

Study 2

Samples derived from 365 well-characterized lung cancer patients (146 adeno-CA, 87 squamous cell CA, 44 small cell CA, 88 other CA of the lung) with the UICC classification given in Table 3 are used

TABLE 3

Study population

| Stage according to UICC | Number of samples |
|---|---|
| UICC I/II | 182 |
| UICC III | 116 |
| UICC IV | 66 |
| unstaged | 1 |
| obviously healthy blood donors | 50 |

Figure 3:
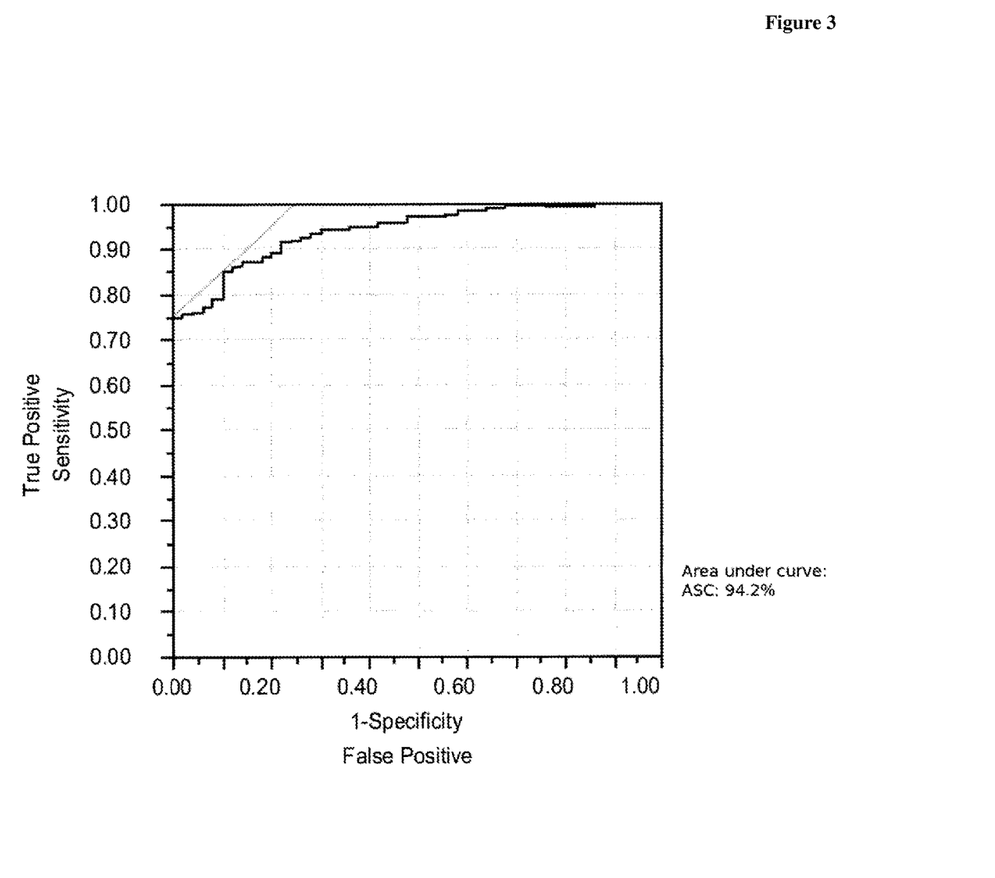
FIG. 3 shows a plot of the receiver operator characteristics (ROC) for the assessment of 365 samples obtained from patients with LC as compared to 50 control samples obtained from obviously healthy individuals.

The level of ASC in the LC samples of Table 3 is evaluated in comparison to 50 control samples obtained from obviously healthy individuals (=control cohort), with an AUC of 0.94 (FIG. 3).

What is claimed is:

1. An in vitro method of screening for an increased level of apoptosis-associated speck-like protein containing a caspase-associated recruitment domain (ASC) associated with presence of lung cancer in a patient, the method comprising:
   selecting a patient who is suffering from or has been previously diagnosed with lung cancer;
   contacting a portion of a sample from the patient with an antibody raised in a nonhuman animal species having specific binding affinity for ASC to form a detectable complex, wherein the antibody is obtained by immunizing the non-human animal species with an antigen comprising a SEQ ID NO: 2-ASC fusion protein;
   detecting and quantifying the detectable complex;
   calculating a concentration of ASC based on the detecting step;
   comparing the calculated concentration of ASC with a reference concentration of ASC;
   calculating a concentration of one or more additional markers for cancer in a portion of a sample from the patient, wherein the one or more additional markers is selected from the group consisting of cytoceratin 19 (CYFRA 21-1), carcinoembryogenic antigen (CEA), neuron-specific enolase (NSE), pro-gastrin-releasing peptide (proGRP), and squamous cell carcinoma antigen (SCC), and
   identifying an increased level of ASC associated with presence of lung cancer in the patient when the calculated concentration of ASC is increased relative to the reference concentration of ASC, and the calculated amount of the one or more additional markers is greater than a reference amount corresponding to each of the one or more additional markers.

2. The method according to claim 1, wherein the one or more additional marker is CYFRA 21-1.

3. The method according to claim 1, wherein the one or more additional marker is CEA.

4. The method according to claim 1, wherein the one or more additional marker is SCC.

5. The method according to claim 1, wherein the sample is a body fluid or a tissue extract.

6. The method according to claim 5, wherein the body fluid is selected from the group consisting of serum, plasma, and blood.

7. The method according to claim 1, wherein the antibody has a binding affinity to ASC of at least $10^7$ l/mol.

8. The method according to claim 1, wherein the antibody is a polyclonal antibody raised in a non-human animal species selected from the group consisting of rabbit, rat, and guinea pig.

9. The method according to claim 1, further comprising conducting one or more additional clinical tests on the patient selected from the group consisting of chest x-ray, computed tomography scan, sputum cytology, and bronchoscopy to confirm presence of lung cancer.

10. An in vitro method of screening for an increased level of apoptosis-associated speck-like protein containing a caspase-associated recruitment domain (ASC) associated with presence of lung cancer in a patient, the method comprising:
    selecting a patient suffering from or at increased risk for lung cancer;
    contacting a portion of a sample from the patient with an antibody having specific binding affinity for ASC to form a detectable complex, wherein the antibody is obtained by immunizing a non-human animal species with an antigen comprising a SEQ ID NO: 2-ASC fusion protein;
    detecting and quantifying the detectable complex; calculating a concentration of ASC based on the detecting step;
    comparing the calculated concentration of ASC with a reference concentration of ASC;
    identifying an increased level of ASC associated with presence of lung cancer in the patient when the calculated concentration of ASC is increased relative to the reference concentration of ASC; and, the increased level of ASC associated with presence of lung cancer in the patient is identified,
    conducting one or more additional clinical tests on the patient selected from the group consisting of chest x-ray, computed tomography scan, sputum cytology, and bronchoscopy to confirm presence of lung cancer.

11. The method according to claim 10, wherein the sample is a body fluid or a tissue extract.

12. The method according to claim 11, wherein the body fluid is selected from the group consisting of serum, plasma, and blood.

13. The method according to claim 10, further comprising calculating an amount of one or more additional markers in a portion of a sample from the patient, wherein the one or more additional markers are selected from the group consisting of cytoceratin 19 (CYFRA 21-1), carcinoembryogenic antigen (CEA), neuron-specific enolase (NSE), pro-gastrin-releasing peptide (proGRP), and squamous cell carcinoma antigen (SCC); comparing the amount calculated with a reference amount corresponding to each of the one or more additional markers selected; and identifying presence of lung cancer in the patient if the calculated amount of the one or more additional markers is greater than a reference amount corresponding to each of the one or more additional markers.

* * * * *